United States Patent [19]

Harden

[11] Patent Number: 4,512,933
[45] Date of Patent: Apr. 23, 1985

[54] APPARATUS FOR DISPENSING VOLATILE SUBSTANCES

[75] Inventor: Theodore A. Harden, Middletown, N.Y.

[73] Assignee: Takasago USA, Inc., Rockleigh, N.J.

[21] Appl. No.: 559,791

[22] Filed: Dec. 9, 1983

[51] Int. Cl.³ .............................................. B01F 3/04
[52] U.S. Cl. .................................... 261/30; 261/104; 261/DIG. 65; 261/81; 239/326
[58] Field of Search .................... 239/326; 261/81, 30, 261/104, DIG. 65

[56] References Cited

U.S. PATENT DOCUMENTS

| | | | |
|---|---|---|---|
| 2,603,468 | 7/1952 | Sutton | 261/30 |
| 2,779,623 | 1/1957 | Eisenkraft | 261/81 |
| 3,522,935 | 8/1970 | Lewis | 261/30 |
| 4,063,826 | 12/1977 | Riepe | 417/410 |
| 4,064,203 | 12/1977 | Cox | 261/99 |
| 4,094,119 | 6/1978 | Sullivan | 53/4 |
| 4,113,809 | 9/1978 | Abair et al. | 261/81 |
| 4,158,440 | 6/1979 | Sullivan et al. | 239/1 |
| 4,166,087 | 8/1979 | Cline et al. | 261/30 |
| 4,271,092 | 6/1981 | Sullivan et al. | 261/30 |
| 4,276,236 | 6/1981 | Sullivan et al. | 261/30 |
| 4,301,095 | 11/1981 | Mettler et al. | 261/30 |
| 4,396,557 | 8/1983 | DeLuca | 261/30 |

OTHER PUBLICATIONS

Piezo Electric Products, Inc., Piezoelectric Quadrature Fan brochure and accompanying data sheets and price list, including data sheets QFA, QFB, QFC, and QFX, 186 Massachusetts Ave., Cambridge, MA 02139, Jul. 21, 1983.

Primary Examiner—Tim Miles
Attorney, Agent, or Firm—Jeffrey H. Ingerman

[57] ABSTRACT

An apparatus is provided for dispensing volatile substances which includes a housing, and at least one piezoelectric blower. Each blower includes a piezoelectric element having a first end mounted to the housing and a second end free, and a generally planar impeller blade connected to the free end of the piezoelectric element and having its distal end unconstrained by the housing. A frame is attached to, or provided as an integral part of, the housing and is located in proximity to the distal end of the blade. The frame is adapted to detachably mount a replaceable substrate cartridge containing a volatile substance. In use, a voltage is applied to the piezoelectric element for oscillating its free end perpendicular to its plane at or close to resonance and propagating a traveling wave along each blade to generate and shed vortices at the distal end of the blade which contact the substrate cartridge, thereby dispensing the volatile substance to the surrounding atmosphere.

20 Claims, 7 Drawing Figures

APPARATUS FOR DISPENSING VOLATILE SUBSTANCES

FIELD OF THE INVENTION

The present invention relates to an apparatus for dispensing volatile substances. More particularly, the present invention relates to an apparatus which employs a piezoelectric blower to dispense a volatile substance.

BACKGROUND OF THE INVENTION

Many products, such as room deodorizers, insecticides, germicides, and the like, are desirably distributed in vapor form in their environment. Products are prepared in solid, semi-solid or liquid form and may be impregnated in porous and microporous materials. The products are released into the environment in which they are located by a vaporization process such as evaporation or sublimation.

Though most products of the type described above are now used merely by exposing them in the environment to be treated, it is preferable in certain applications to induce greater distribution of the product than is possible by this technique. If an apparatus is provided to induce this greater distribution, it is desirable to house the apparatus compactly and conveniently so that when exhausted, the product can be easily replenished and so that access to the components of the apparatus may be easily provided. The apparatus should also be mountable in small areas yet still offer the above features.

Reported Developments

Systems for providing air currents that contact vaporizable products to assure greater and more even product distribution are known, as evidenced by the following patents.

U.S. Pat. No. 4,064,203 discloses an air-circulating device having an upright tube or passage and a fan for drawing warm air downward from adjacent the ceiling of a room and discharging it adjacent the floor. The device is provided with a liquid reservoir and a wick, with the wick positioned in the circulating air to provide air freshening and humidifying. The reservoir may be adjacent the tube above the fan or may be adjacent the fan outlet. A further modification provides a charcoal or other type filter in the air stream to remove odors, such as cigarette smoke.

U.S. Pat. Nos. 4,271,092 and 4,276,236 disclose a battery-powered apparatus for inducing air flow past a product capable of being vaporized. The apparatus includes a compact housing that comprises a hollow outer shell and a hollow, generally cylindrical inner shell, having an axis, on which the operating components of the apparauts are supported. The inner shell is mounted within the outer shell by a hinge to pivot substantially on the axis between closed and open positions. In the closed position the inner shell complements the outer shell to define an enclosed space and shield the components of the apparatus. In the open position, the inner shell is nested within the outer shell to expose the components of the apparatus.

U.S. Pat. No. 4,301,095 discloses a room air freshener device that operates to propel air which has been induced by a fan, past a cartridge comprising a pad impregnated with a readily volatilizable fluid. The air moves past and through the cartridge, to volatilize the liquid, delivering it to the environment.

U.S. Pat. No. 4,396,557 discloses an evaporative dispenser for emitting a vaporized material into the ambient. A battery powered, motor-driven fan forces air through the dispenser housing and across a material reservoir to evaporate and entrain material therein prior to being discharged from the housing. A supply container is supported directly on a reservoir lid and comprises structure which cooperates with the housing to direct the air flow across the reservoir. The supply container also comprises a battery nesting recess which affords compact packaging of the components within the housing. A transparent viewing window is provided for easy viewing of the level of material in the reservoir.

SUMMARY OF THE INVENTION

An apparatus is provided for dispensing volatile substances which includes a housing, and at least one piezoelectric blower; preferably two blowers. Each blower includes a piezoelectric element having a first end mounted to the housing and a second end free, and a generally planar impeller blade connected to the free end of the piezoelectric element and having its distal end unconstrained by the housing. The blade preferably has a high Q-factor, a high stiffness-to-weight ratio and a low mass per unit area which is substantially less than that of the piezoelectric element. When two piezoelectric elements and blades are employed, the blades preferably are mounted within the housing in spaced relationship such that the planes of the blades are generally parallel and such that the distal end of each blade protrudes from and is unconstrained by the housing. A frame is attached to or provided as an integral part of the housing and is located in proximity to the distal end of the blade or blades. The frame is spaced from the housing a distance greater than the distance that the blades protrude from the housing and defines an opening which lies in a plane substantially perpendicular to the blades. The frame is adapted to detachably mount a replaceable substrate cartridge containing a volatile substance. In use, a voltage is applied to each piezoelectric element for oscillating its free end perpendicular to its plane at or close to resonance and propagating a traveling wave along each blade to generate and shed vortices of air at the distal ends of the blades which contact the substrate cartridge mounted in the frame, thereby dispensing the volatile substance to the surrounding atmosphere. The apparatus may include timing means either preset or adjustable which when actuated operate the piezoelectric blower for a set period of time, indicator means for giving a visual indication that the substrate has been depleted of its supply of volatile substance and should be replaced, and may also include filtration means.

BRIEF DESCRIPTION OF THE DRAWINGS

FIG. 1 is an elevational view, in perspective, of an embodiment of an apparatus of the present invention for dispensing volatile substances.

FIG. 2 is a front view of the apparatus of FIG. 1 showing, in phantom, the travel of the impeller blades.

FIG. 3 is a pictorial view of a piezoelectric blower.

FIG. 4 is a longitudinal-sectional view of a piezoelectric bilaminate driving element for use in the blower shown pictorially in FIG. 3.

FIG. 5 is a pictorial view of another embodiment of a piezoelectric blower.

FIG. 6 is a partially fragmentary perspective view of a substrate cartridge for use in the apparatus shown in FIG. 1.

FIG. 7 is a partial fragmentary perspective view of another embodiment of a substrate cartridge for use in the apparatus shown in FIG. 1.

The present invention will now be described with reference to FIGS. 1 through 7 in which like parts are given like reference numerals throughout.

DESCRIPTION OF THE PREFERRED EMBODIMENT

Figure 1:
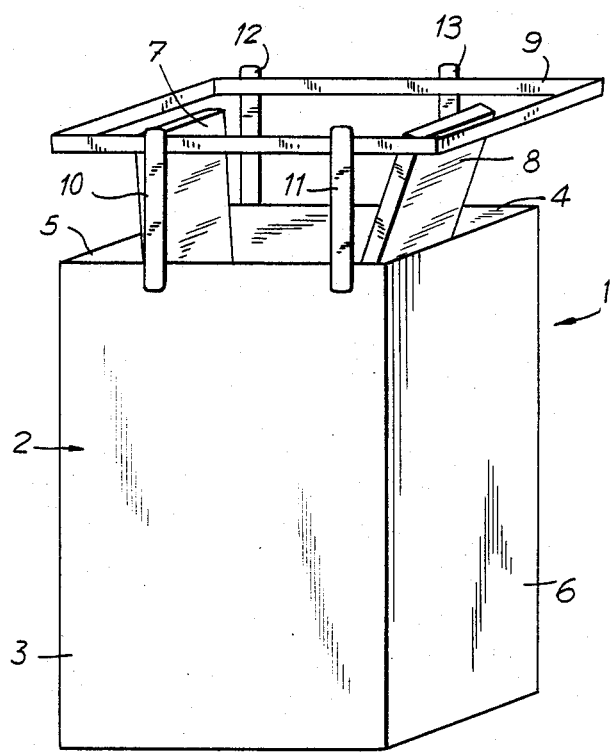
Figure 2:
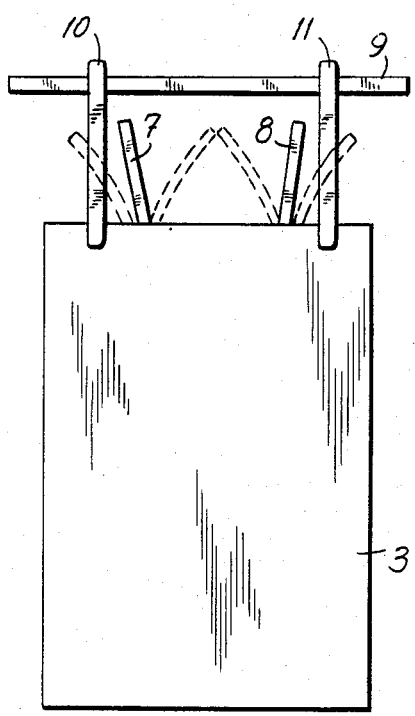

Referring to FIG. 1 and FIG. 2, an apparatus for dispensing volatile substances is shown. Apparatus 1 includes a housing 2 which consists of front wall 3, back wall 4 and side walls 5 and 6 joined at their edges to form a substantially rectangular structure. Housing 2 is exemplary only and various other configurations may be employed including a cylindrical housing or a rectangular housing in which one or more of the walls is omitted. As shown in FIG. 1 and FIG. 2, the housing has an open side through which impeller blades 7 and 8 protrude. Preferably, the opposite side is left open to permit air to enter the housing but this opposite side may be closed in which case air inlet ports may be provided in one or more sides of housing 2.

Figure 3:
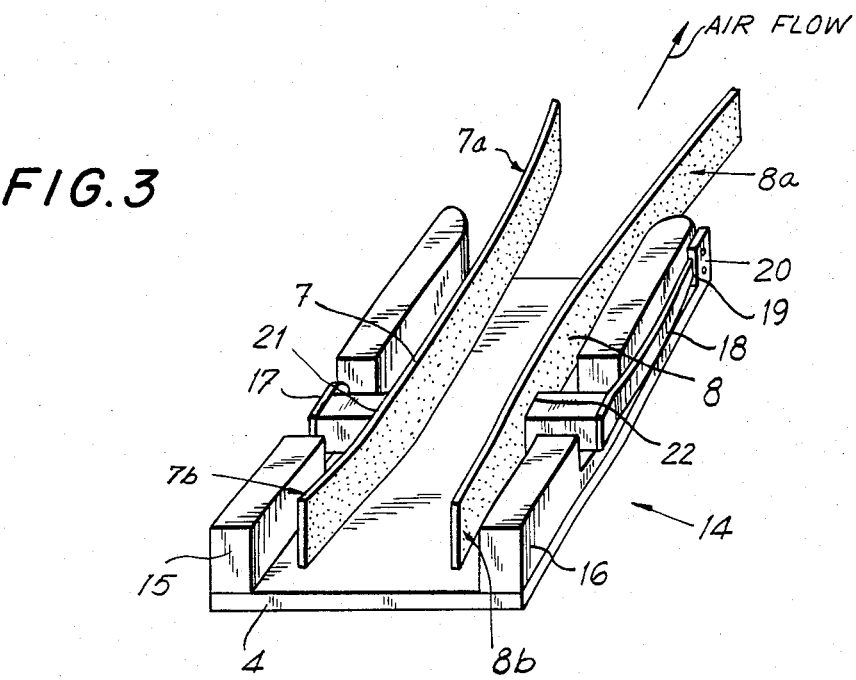
Figure 5:
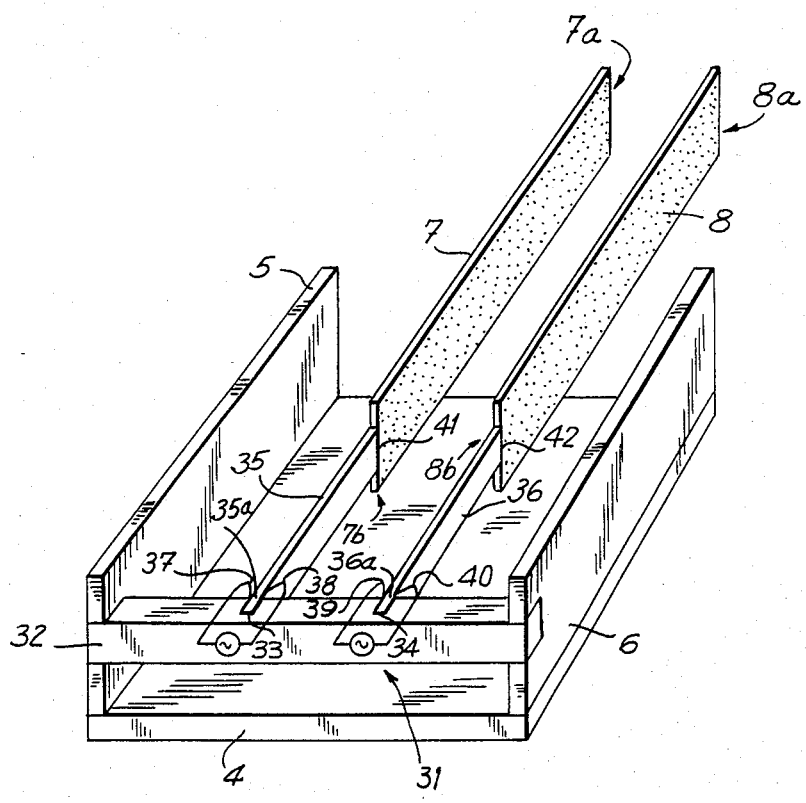

Impeller blades 7 and 8 are connected to piezoelectric elements as part of a piezoelectric blower assembly, examples of which are shown in FIG. 3 and FIG. 5 and described below with reference to FIG. 3 and FIG. 5. The piezoelectric blower assembly is attached to housing 2. The blades 7, 8 are generally planar and are mounted within the housing such that the planes are generally parallel to each other.

The apparatus includes a frame 9 defining an opening which lies in a plane substantially perpendicular to and preferably centered over blades 7 and 8. As shown in FIG. 1 and FIG. 2, the frame is rectangular but a circular or other shaped frame may desirably be employed. It is preferred for optimum operation of the apparatus that the frame be located so that the substrate cartridge is centered over the blades to receive the full benefit of the vortices shed by the blades. Frame 9 is spaced from the housing 2 a distance greater than the distance that the blades protrude from the housing. As shown in FIG. 1 and FIG. 2, the frame is attached to the housing by rigid supports 10, 11, 12 and 13. The frame is adapted to detachably mount a replaceable substrate cartridge containing a volatile substance. The substrate cartridge will typically be about the same shape and size as the opening in the frame and may be retained therein by any suitable means including friction, clamps, or the like. The housing, supports, and frame may be made of the same or different materials and will preferably be made of a plastic or metal.

In use, a voltage is applied to the piezoelectric element attached to blade 7 and the piezoelectric element attached to blade 8 causing the free end of each element to oscillate perpendicular to its plane at or close to resonance thereby propagating a traveling wave along each blade to generate and shed vortices at the distal ends of the blades which contact the substrate cartridge mounted in the frame, thereby dispensing the volatile substance to the surrounding atmosphere. In FIG. 2 is shown, in phantom, the travel of blades 7 and 8.

The apparatus of the present invention may be employed as a wall unit, or a table unit. Accordingly, the housing 2 may be fitted with a base, if desired, or may include means for attaching the apparatus to a surface, such as a wall. Electrical connections may be provided in the form of a cord or a standard male electrical plug mounted in one of the walls of housing 2 such that the male plug may be inserted in a standard female outlet, whereby electrical connection is provided and the apparatus is thereby attached to the surface containing the outlet.

The apparatus may be directly connected to a current source for continuous operation or may include integral means for selectively operating the apparatus. Accordingly, the apparatus may include a simple switch, a sound actuated switch, timing means which, when actuated, operate the apparatus for a preset period of time, indicator means for providing a visual signal, audible signal or both to advise the user that the substrate has been depleted of its supply of volatile substance and should be replaced or that the apparatus has been in operation for a set period of time, means to vary the output of the blower, or similar such variations as may occur to those skilled in the art.

The apparatus of the present invention employs a piezoelectric blower, examples of which are shown in FIGS. 3 and 5. The blower employs piezoelectric elements attached to impeller blades. The piezoelectric element or bilaminate applies a sinusoidal driving force to the blade for propagating a traveling flexure wave along the blade, preferably in a quadrature relation. The entire length of the blade is thus free to move laterally as it is driven back and forth by the piezoelectric element. The piezoelectric bilaminate is a strip consisting of two layers of piezoelectric ceramic polarized in opposite directions which on their facing sides are separated by a conducting layer and on their outside faces are surrounded by conducting layers. The two outside conducting layers are connected as electrodes to a controlled alternating current supply. Since the piezoelectric layers have opposite polarity, voltage applied across the bilaminate strip induces bending of the element. Accordingly, alternating voltage across the piezoelectric element drives the blade back and forth at the point of attachment. More than two layers of ceramic may be used if desired, and connected in parallel to lower the operating voltage. The blower operates without any substantial mechanical friction to permit high operating speed, high throughput relative to size, and virtually unlimited service life and preferably is constructed with a pair of counter-oscillating blades in parallel so that it is dynamically balanced and vibration free.

Referring to FIG. 3, a piezoelectric blower assembly 14 is shown mounted within housing 2. Outer walls 3, 5 and 6 of housing 2 have been removed for clarity. A pair of resilient blades 7, 8 having outlet ends 7a, 8a and inlet ends 7b, 8b are mounted in housing 2 employing lateral supports 15, 16 which are attached to wall 4 of housing 2.

A pair of piezoelectric bilaminates 17, 18 are attached at one end 19, for example by a plastic holder and screws 20, to each of the supports 15, 16 and at the other ends 21, 22, by cementing or any other suitable means, to a point on each blade 7, 8 to support the blades in the housing 2, in a manner such that upon lateral movement of the bilaminates, the blades 7, 8 are free to undergo simultaneous lateral deflection. This mounting arrangement permits free lateral movement of the blades 7, 8 along the entire length with corresponding lateral movement of the ends 17, 18 of the piezoelectric elements 17, 18.

Figure 4:
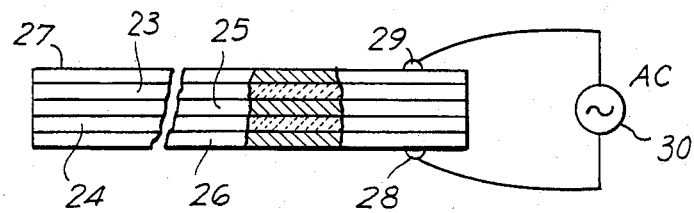

A piezoelectric element suitable for use in the present invention is marketed by Piezo Electric Products, Inc., Metuchen, N.J., under the name "Piezo Ceramic Bender Element, No. G1195". Each bilaminate strip 17, 18, as shown in FIG. 4, has two layers of piezoelectric ceramic 23, 24 separated by a layer of conducting material 25, e.g. brass. The outside layers 26, 27 are conducting (e.g., nickel, silver) and connected to the leads 28, 29 of a controlled alternating current supply 30. The two ceramic layers 23, 24 are polarized in opposite directions, so that voltage across the bilaminate induces a bending motion in the strip. Since, as illustrated with respect to bilaminate strip 18 in FIG. 3, each strip is fixed to the housing, as at 20, controlled alternating voltage causes the free end 22 of the piezoelectric element to move back and forth at the voltage frequency. The bending movement of the bilaminates 17, 18, in turn, drives the blades 7, 8 back and forth at the point of attachment 21, 22 at a controlled rate. Although not illustrated in FIG. 3, the connections from the piezoelectric elements 17, 18 to the power supply 30, FIG. 4, are conveniently made at the end 19, beneath the holder 20.

When driven back and forth, each blade 7, 8 represents a beam subjected to combined bending and shearing loads varying so rapidly that inertial effects dominate to propagate a traveling flexure wave along the impeller or blade from the inlet end to the outlet end. Typically a voltage oscillating in the range of from about 60 to about 400 Hz. is applied. The most efficient pumping action results when the driving force is applied in quadrature, that is, to produce a 90 degree phase lag in the oscillation cycle between two points along the blade. In the embodiment shown in FIG. 3, the piezoelectric blower contains two counter-oscillating blades 7, 8 to operate 180 degrees out of phase with each other. The complementary back and forth motion of the two blades 7, 8 provides dynamic balancing and prevents vibration of the device.

A second embodiment of the piezoelectric blower illustrated in FIG. 3 is shown in FIG. 5, where in place of the side mounted piezoelectric elements 17 and 18 of the embodiment shown in FIG. 3, a pair of end-mounted bilaminate piezoelectric elements 35, 36 drive respective, flat, resilient blades 7 and 8. The blower assembly 31 is mounted in housing 2 employing side walls 5 and 6 and a cross member 32 which extends between and is attached to side walls 5, 6 of housing 2. The piezoelectric bilaminates 35, 36 are mounted at one end 35a, 36a to cross member 32. The member 32 is provided with a pair of vertical slots 33, 34, each of which is sized to snugly receive a respective end 35a, 36a of the bilaminates 35, 36 and respective pairs of electrically conductive contact leaves 37, 38 and 39, 40, one leaf on each side of the bilaminates. Conductors, not shown, are connected to the leaves for coupling to the alternating voltage supply. The free ends of the bilaminates are attached at junctions 41, 42 to resilient blades 7, 8.

In this mounting arrangement, as in the FIG. 3 embodiment, the blades 7, 8 are not fixed at any point relative to the housing 2 and each blade is free to move laterally, that is, perpendicular to the flat surface of the blade, back and forth along its entire length when driven by the free end of the piezoelectric element. As in the case of the blade in FIG. 3, when alternating voltage is applied across the bilaminates 35, 36, a cyclical back and forth movement occurs in the free ends of the bilaminates which in turn drives the ends of the blades 7, 8 at junctions 41, 42 back and forth in the housing 2. Since the entire length of each blade 7, 8 is free to move back and forth relative to the housing 2 a traveling flexure wave is propagated when each blade is driven at an appropriate frequency. Since, however, the propagated wave travels along each blade from one end 7b, 8b to the other 7a, 8a, the blower works very efficiently in pumping fluids, especially air, without the need for valving action. To effect dynamic balancing of the system, the two bilaminates are driven in opposing phase relationship, as in the FIG. 3 embodiment. Although for dynamic balancing purposes, it is preferable to employ a pair of counter oscillating blades, the embodiments of both FIGS. 3 and 5 can provide effective air movement with a single oscillating blade.

The combined system of the piezoelectric element and the blade should have its resonant frequency equal or approximately equal to the frequency of the applied voltage to an accuracy typically within plus or minus 2% or within $1\frac{1}{4}$ Hz. at a resident frequency of 60 Hz. The blades may be attached to the piezoelectric element by any suitable means such as by means of a cemented lap joint, or by the use of a slotted junction block.

No ducts, walls or valving are required for the operation of the blower. In fact, the blades operate best in free air completely unobstructed. Valving action or flow rectification is accomplished with a process of vortex shedding from the blade tip. Vortex shedding is a process whereby air is prevented from being sucked around the blade tip when motion reverses. It is based on the fact that air displaced from the front of a moving blade rotates so rapidly that it is unable to reverse its direction of rotation when the blade reverses its motion. If the rotation is not sufficiently rapid, the vortex can reverse its direction of rotation to be sucked around the blade tip instead of leaving the blade. Vortex shedding is enhanced by, but does not require, exact quadrature motion; that is a 90 degree lag between the root and tip of the blade. In this way, a line of oppositely rotating vortices is generated resulting in a highly directional stream of air. If this vortex shedding effect is disturbed by obstructions in the area, the air simply flows from the forward surface of the blade around its trailing edge to the rearward surface of the blade when the motion reverses. There is then only circulation around the trailing edge and very little outward flow.

While normal piezoelectric elements have amplitudes of several thousandths of an inch, typically from 0.01 inch to 0.02 inch, the blower blades employed in this invention provide amplitudes on the order of one inch. The material out of which the blade is constructed must have low internal damping. Internal damping is a measure of the elasticity of the material, usually expressed in terms of a "Q-factor" which is simply the ratio of peak elastic energy stored to total energy lost during one deformation cycle. In quantitative terms, a perfectly elastic tennis ball would rebound to the same height from which it was dropped. If it rebounded to 90% of the height, it is said to have a Q-factor of 10. One-tenth of the peak energy stored is lost during impact. If it rebounds to half the height, its Q-factor would be 2, half the energy lost. If it landed with a thud like a piece of clay and did not rebound at all, its Q-factor would be unity; all the stored energy would have been dissipated. For effective blowing action, the blade material should have a Q-factor of at least 8 to 10. Various metals satisfy this requirement, for example, hard brass, phosphor-bronze, beryllium, copper alloy, steel.

The blade material should have a high stiffness-to-weight ratio. The minimum stiffness-to-weight ratio can be defined as a ratio of Young's modulus over density greater than one million newton-meters per kilogram. Young's modulus is defined as the slope of the stress versus strain curve within the elastic range and has the dimensions of stress over strain, notably newtons per square meter over meters per meter, while density has the dimensions of kilograms per cubic meter; thus the requirement can be expressed as Young's modulus/density greater than one million newton-meters per kilogram.

The blade should also have a low mass compared to the piezoelectric element. If the mass of the blade is too high, it will cause the element to break when the blade is driven to a high resonant amplitude and there will not be a discontinuity at the point where the blade joins the piezoelectric element. For a blade of uniform width and thickness, the maximum mass per unit area of the blade is usually no more than 50 to 60% of the mass per unit area of the element. Two materials have been found to work very well for the blade, Mylar and G-10. The following table presents the stiffness, density and stiffness/density ratio of a number of blade materials, including Mylar and G-10.

| MATERIAL | BLOWER BLADE MATERIALS PROPERTY TABULATION | | |
|---|---|---|---|
| | STIFFNESS $(Nt/M^2)$ | DENSITY $(Kg/M^3)$ | STIFFNESS/ DENSITY RATIO $(NtM/Kg)$ |
| Steel | $20 \times 10^{10}$ | $7.83 \times 10^3$ | $2.55 \times 10^7$ |
| Brass | $9 \times 10^{10}$ | $8.56 \times 10^3$ | $1.05 \times 10^7$ |
| G-10 | $1.9 \times 10^{10}$ | $1.9 \times 10^3$ | $1.0 \times 10^7$ |
| Mylar | $0.379 \times 10^{10}$ | $1.39 \times 10^3$ | $0.272 \times 10^7$ |
| Lexan | $0.199 \times 10^{10}$ | $1.2 \times 10^3$ | $0.166 \times 10^7$ |
| Polyethylene (High Dens.) | $0.11 \times 10^{10}$ | $0.96 \times 10^3$ | $0.114 \times 10^7$ |
| Polyethylene (Low Dens.) | $0.026 \times 10^{10}$ | $0.91 \times 10^3$ | $0.028 \times 10^7$ |

Figure 6:
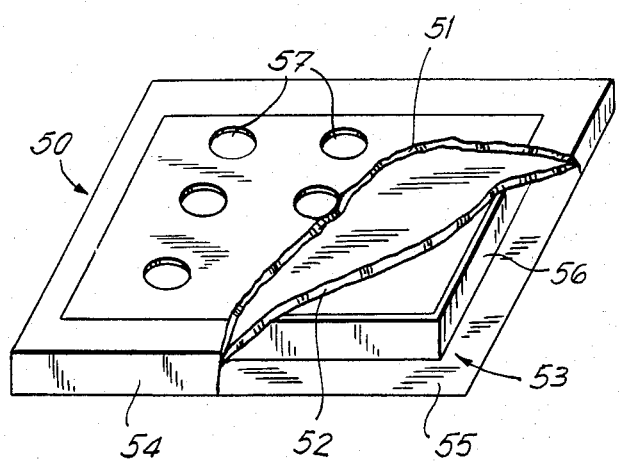
Figure 7:
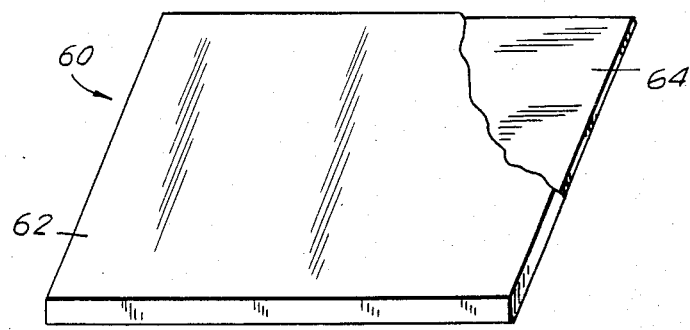

Two embodiments of the replaceable or disposable substrate cartridge are shown in FIG. 6 and FIG. 7, respectively. As shown in FIG. 6, the substrate cartridge 50 is rectangular and sized to fit the opening in frame 9. Other configurations may also be employed depending on the shape and size of the frame or other mounting means. Cartridge 50 includes a barrier layer 51, a membrane layer 52, and a reservoir 53. The reservoir is a three-sided channel formed by walls 54, 55 and 56. The fourth side is covered by membrane layer 52 and barrier layer 51. Barrier layer 51 includes a plurality of openings 57. In practice, reservoir 53 is filled with a volatile substance which diffuses through and is absorbed by membrane 52. Barrier layer 51 functions to control the rate at which the volatile substance is released by the membrane layer 52. Increasing the number of openings 57, increases the rate at which the volatile substance is released. In operation, the vortices discharged by the blades contact membrane material 52, pass through the membrane and exit through openings 57 in layer 51 carrying along the volatile substance which has diffused into membrane 52. If desired, the vortices may pass through the cartridge in the opposite direction. The reservoir is preferably vacuum formed from a rigid polyester; more preferably from a clear polyester sheet about 0.05 mm thick. The use of a clear polyester or other such material permits a visual determination of the amount of volatile substance remaining in reservoir 53. Membrane layer 52 is preferably fabricated from a polyester fiber pressed into a non-woven sheet containing irregular channels for absorption and surface evaporation of the volatile substance, and the density of the non-woven material can be selected to define the absorption rate for the volatile substance. Barrier layer 51 is preferably a clear, polyester sheet perforated with openings 57. Various modifications of cartridge 50 will be apparent to those skilled in the art and are included within the scope of the present invention. For example, barrier layer 51 may be omitted.

In FIG. 7 is shown a replaceable substrate cartridge 60 which is sized to fit the opening in frame 9 and which includes an outer membrane material 62, and an inner material 64 impregnated with a volatile substance. Material 64 is an absorbent, porous material such as cellulose, felt, porous plastic, cellular blotter board or the like, and membrane material 62 is preferably a microporous membrane of a suitable polymer which permits the volatile substance to diffuse outward through the membrane. A preferred membrane material is an isostatic polypropylene film containing pores less than a micron in diameter, typically about 0.02 micron. Preferably, the membrane 62 is in contact with material 64 over a substantial portion of its interior surface. Material 64 may be sealed within membrane 62 by heat sealing or other suitable means. The rate of diffusion may be adjusted by heat-sealing portions of the surface of the membrane to reduce the pore density. Various modifications will occur to those skilled in the art and are included within the scope of this invention. For example, the membrane material may be a material which is transparent when saturated with the volatile substance but which is opaque when not saturated, thus providing a visual determination of the level of volatile substance remaining in cartridge 60.

It will be understood that the particular embodiments described above are only illustrative of the principles of the invention, and that various modifications can be made by those skilled in the art without departing from the scope and spirit of the invention. For example, the opening between frame 9 and housing 2 may be covered with an air-permeable material such as a screen, or apparatus 1 may include air filtration means.

I claim:

1. An apparatus for dispensing volatile substances, comprising a housing, a piezoelectric element having one end mounted to the housing and one end free, a generally planar impeller blade connected to the free end of the piezoelectric element and having its distal end unconstrained by the housing, means for detachably mounting a replaceable substrate cartridge containing a volatile substance in proximity to the distal end of the impeller blade, and means for applying a voltage to the piezoelectric element for oscillating its free end perpendicular to its plane at or close to resonance and propagating a traveling wave along the blade to generate and shed vortices at the distal end of the blade, such that the vortices contact the substrate cartridge, thereby dispensing the volatile substance.

2. The apparatus of claim 1 wherein the traveling wave propagated along the blade is a quadrature wave.

3. The apparatus of claim 1 wherein the means for detachably mounting the substrate cartridge comprises a frame attached to the housing in proximity to the distal end of the blade, and adapted to detachably mount the replaceable substrate cartridge.

4. The apparatus of claim 3 wherein the frame defines an opening in a plane substantially perpendicular to the blade.

5. The apparatus of claim 3 wherein the frame is an integral part of the housing.

6. An apparatus for dispensing volatile substances, comprising a housing, first and second spaced piezoelectric elements each having one end mounted to the housing and one end free, first and second generally planar impeller blades connected, respectively, to the free ends of the first and second piezoelectric elements and each having its distal end unconstrained by the housing, means for detachably mounting a replaceable substrate cartridge containing a volatile substance in proximity to the distal ends of the impeller blades, and means for applying a voltage to each piezoelectric element for oscillating its free end perpendicular to its plane at or close to resonance and propagating a traveling wave along each blade to generate and shed vortices at the distal end of each blade, such that the vortices contact the substrate cartridge, thereby dispensing the volatile substance.

7. The apparatus of claim 6 wherein the traveling waves propagated along the blades are quadrature waves.

8. The apparatus of claim 6 wherein the first and second blades have a high Q-factor, a high stiffness-to-weight ratio and a mass per unit area substantially less than that of the first and second piezoelectric elements, respectively.

9. The apparatus of claim 6 wherein the first and second blades are mounted within the housing in spaced relationship such that the planes of the blades are generally parallel and such that the distal end of each blade protrudes from and is unconstrained by the housing.

10. The apparatus of claim 6 wherein the means for detachably mounting the substrate cartridge comprises a frame attached to the housing in proximity to the distal ends of the blades, and adapted to detachably mount the replaceable substrate cartridge.

11. The apparatus of claim 10 wherein the frame defines an opening in a plane substantially perpendicular to the blades.

12. The apparatus of claim 10 wherein the frame is an integral part of the housing.

13. An apparatus for dispensing volatile substances, comprising a housing a piezoelectric element having one end mounted to the housing and one end free, a generally planar impeller blade connected to the free end of the piezoelectric element and having its distal end unconstrained by the housing, the blade having a high Q-factor, a high stiffness-to-weight ratio and a mass per unit area substantially less than that of the piezoelectric element, means for detachably mounting a replaceable substrate cartridge containing a volatile substance in proximity to the distal end of the impeller blade, and means for applying a voltage to the piezoelectric element for oscillating its free end perpendicular to its plane at or close to resonance and propagating a traveling wave along the blade to generate and shed vortices at the distal end of the blade, such that the vortices contact the substrate cartridge, thereby dispensing the volatile substance.

14. The apparatus of claim 13 wherein the traveling wave propagated along the blade is a quadrature wave.

15. The apparatus of claim 13 wherein the Q-factor is at least eight.

16. The apparatus of claim 13 wherein the stiffness-to-density ratio of the blade is more than one million newton-meters per kilogram.

17. The apparatus of claim 13 wherein the blade and the piezoelectric element are of uniform width and thickness and the mass per unit area of the blade is less than 60% of the mass per unit area of the piezoelectric element.

18. The apparatus of claim 13 wherein the means for detachably mounting the substrate cartridge comprises a frame attached to the housing in proximity to the distal end of the blade, and adapted to detachably mount the replaceable substrate cartridge.

19. The apparatus of claim 18 wherein the frame defines an opening in a plane substantially perpendicular to the blade.

20. The apparatus of claim 18 wherein the frame is an integral part of the housing.

* * * * *